United States Patent
Doswald et al.

(10) Patent No.: US 7,196,234 B2
(45) Date of Patent: Mar. 27, 2007

(54) ASYMMETRIC REDUCTION OF 1,1,1-TRIFLUOROACETONE

(75) Inventors: Stephan Doswald, Reinach (CH); Steven Paul Hanlon, Bottmingen (CH); Ernst Kupfer, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/478,821

(22) Filed: Jun. 30, 2006

(65) Prior Publication Data
US 2007/0009999 A1    Jan. 11, 2007

(30) Foreign Application Priority Data
Jul. 8, 2005    (EP)    ................... 05106261

(51) Int. Cl.
*C07C 29/14*    (2006.01)
(52) U.S. Cl. .................................................... 568/880
(58) Field of Classification Search ................ 568/880
See application file for complete search history.

(56) References Cited
OTHER PUBLICATIONS

Crawford, J. W. C., Journal of the Chemical Society (C) (1967) pp. 2332-2333.
Rosen, T. C. et al., Chiral Catalysis (2004) Suppl, 43-45.
Bucciarelli M., et al., Synthesis (1983) 11, pp. 897-899.
Dahl A. C. et al., Tetrahedron: Asymmetry (1999) 10, pp. 551-559.
Yasohara Y., et al., Appl. Microbiol. Biotechnol. (1999) 51: 847-851.
Yang, Z.-H., et al., Ind. Eng. Chem. Res. (2004) vol. 43, pp. 4871-4875.
Nakamura, K. et al., Tetrahedron: Asymmetry (1996), vol. 7, pp. 409-412.

*Primary Examiner*—J. Parsa
(74) *Attorney, Agent, or Firm*—George W. Johnston; Patricia S. Rocha-Tramaloni; Kimberly J. Prior

(57) ABSTRACT

The invention relates to a scalable biocatalytic process for the preparation of S-1,1,1-trifluoro-2-propanol with a enantiomeric excess of >99% by asymmetric microbial reduction of 1,1,1-trifluoroacetone with Baker's yeast.

10 Claims, No Drawings

ASYMMETRIC REDUCTION OF 1,1,1-TRIFLUOROACETONE

PRIORITY TO RELATED APPLICATIONS

This application claims the benefit of European Application No. 05106261.0, filed Jul. 8, 2005, which is hereby incorporated by reference in its entirety.

FIELD OF THE INVENTION

The present invention relates to the preparation of enantiomerically pure (S)-1,1,1-trifluoro-2-propanol (>99% enantiomeric excess) with a biocatalyst by an asymmetric reduction of 1,1,1-trifluoroacetone.

BACKGROUND OF THE INVENTION

J. W. C. Crawford (1967), *J. Chem. Soc.* (C) 2332–2333, described a method for producing (S)-1,1,1-trifluoro-2-propanol, where (±)-1-(trifluoromethylethoxy) propionic acid (the adduct of the alcohol and acrylic acid) was separated into its optical isomers through its quinine salt, and pure (S)-1,1,1-trifluoro-2-propanol was obtained from the enantiomeric pure alkoxy-acid by alkaline hydrolysis and distillation. Although this method affords (S)-1,1,1-trifluoro-2-propanol of high enantiomeric purity (optical rotation: −5.65°), the method is not suitable for large scale production.

T. C. Rosen et al. (2004), *Chimica Oggi Suppl.*, 43–45, prepare both (R)- and (S)-1,1,1-trifluoro-2-propanol by asymmetric reduction of 1,1,1-trifluoroacetone using alcohol dehydrogenases (ADHs) either in their natural hosts or as recombinant enzymes expressed in *E. coli*. Resting whole cells or crude cell free extracts may be used and in the latter case addition of a cofactor regenerating system is necessary. The resulting (S)-1,1,1-trifluoro-2-propanol is available for purchase at Jülich Fine Chemicals, but the material offered is of insufficient enantiomeric purity (>92.5% ee) for our needs.

M. Buccierelli et al. (1983), *Synthesis* 11, 897–899, describe the preparation of (S)-1,1,1-trifluoro-2-propanol by reduction of 1,1,1-trifluoroacetone using (resting) Baker's yeast on lab scale. Although the reaction proceeds fast (4 hours), a 300 times excess of yeast with respect to substrate is required, the substrate concentration is only 2.5 g/kg yeast suspension, and (S)-1,1,1-trifluoro-2-propanol is obtained only with approx. 80% ee (as calculated from the optical rotation of −4.5° for the isolated alcohol, compared with −5.6° for the pure alcohol), a value which is far too low for our needs. In addition, the isolation protocol, based on repeated solvent extraction in combination with distillation, is not applicable economically on large scale.

There are several methods used in literature to optimize the stereoselectivity of microbial reductions, e.g. acetone treatment of the microbial cells or performing the biotransformation in organic solvents. Both methods have the disadvantages that using solvents makes a process more costly and, more important, the solvent used further complicates the already demanding procedure for the isolation of (S)-1,1,1-trifluoro-2-propanol, which possesses a boiling point of 76–77 °C.

Another method to increase the stereoselectivity is using inhibitors to block the enzyme(s) affording the unwanted isomer. A. C. Dahl et al. (1999), *Tetrahedron: Asymmetry* 10, 551–559, reported the reduction of ethyl-3-oxopentanoate with non heat-treated Baker's yeast and allyl alcohol to ethyl-3(R)-hydroxy-pentanoate (100% yield and 92–93 % ee). When heat-treated Baker's yeast (48° C. for 60 min) was used in combination with allyl alcohol the product was obtained in 80–95% yield and the ee was increased to 98%. However, for the successful reaction a substrate concentration of approximately 1 g/L was used and 250 times yeast relative to substrate, respectively 4 times inhibitor relative to substrate were required.

Another method to influence the stereoselectivity of a microbial reduction is to perform a heat treatment of the microbial cells, to inactivate the enzymes affording the non-wanted stereoisomer. Y. Yasohara et al. (1999), *Appl. Microbiol. Biotechnol.* 51, 847–851, investigated the reduction of ethyl 4-chloro-3-oxobutyrate (COBE) to 4-chloro-(S)-3-hydroxybutyrate (CHBE) with various yeasts. Acetone treated cells of *Candida magnolia* converted COBE in 75% molar yield to (S)—CHBE with 91.0% ee. When the cells of *C. magnolia* were heat treated (60° C.), (S)—CHBE was obtained in 75% yield with >98% ee. On the other side, when acetone treated cells of *Saccharomyces cerevisiae* were used (non-heat treated), (S)—CHBE was obtained in 53% molar yield and only with 14.8% ee. After heat treatment cells of *S. cerevisiae* at 50° C., (S)—CHBE was obtained in only 10% yield with 53.8% ee. (S)—CHBE was obtained with >98% ee after heat treatment at 60° C. (8% yield). On a preparative scale, using *C. magnoliae*, 90 g/L COBE was converted quantitatively to (S)—CHBE with 96.6% ee within 60 hours, respectively in 97% yield and with >99% ee, using heat treated cells. The reaction was performed in a two phase system with n-butyl acetate and required a coenzyme-regenerating system (glucose, NAD(P) and glucose dehydrogenase). The requirement for a cofactor regenerating system based on glucose dehydrogenase is due to inactivation of endogenous enzymes by acetone treatment.

Z. H. Yang et al (2004), *Ind. Eng. Chem. Res.* 43, 4871–4875, described also the asymmetric reduction of COBE to (S)—CHBE catalyzed by yeast. By heat treatment of the yeast (50° C.) the ee of (S)—CHBE increased from 84% to 97%, with an increase in the pretreatment time from 30 to 120 min. On the other hand the conversion of COBE decreased from 96% to 82%. Glucose was used to regenerate NAD(P) to NAD(P)H. The reaction was performed with yeast from dried baker's yeast. The described procedure is not useful and economic for using on large scale.

K. Nakamura et al. (1996), *Tetrahedron: Asymmetry* 7, 409–412, described the yeast reduction of α-diketones to the corresponding hydroxyketo compounds, where the heat treatment influenced the regioselectivity of the reaction. Although, for example, the reduction of 1-phenyl-1,2-propanedione with heat treated yeast afforded 1-phenyl-2-hydroxy-1-propanone in 80% yield and >98% ee, the reaction required a relatively large amount of yeast (30 times relative to the substrate).

SUMMARY OF THE INVENTION

The present invention provides an efficient procedure for producing (S)-1,1,1-trifluoro-2-propanol of high enantiomeric purity (>99% ee). In particular, the present invention provides a method for preparing enantiomerically pure (S)-1,1,1-trifluoro-2-propanol (>99% enantiomeric excess) with a biocatalyst by an asymmetric reduction of 1,1,1-trifluoroacetone.

The enantiomerically pure (S)-1,1,1-trifluoro-2-propanol is an important building block for the preparation of isomerically pure active pharmaceutical ingredients (APIs) used for the treatment of neurological and neuropsychiatric disorders.

For the preparation of APIs it is important to use isomerically pure building blocks and/or highly stereoselective procedures because side components in APIs may have adverse effects in the treatment of illnesses. Therefore, a high purity is requested for all APIs.

The present invention provides a method for preparing enantiomerically pure (S)-1,1,1-trifluoro-2-propanol with an enantiomeric excess (ee) of >99%, which may be used as a key building block for the preparation of enantiomerically pure APIs, for example, those described in WO 2005/014563. As the enantiomeric purity of neither the building block (S)-1,1,1-trifluoro-2-propanol nor its subsequent intermediates in the syntheses towards the respective APIs can be enriched it is paramount to use (S)-1,1,1-trifluoro-2-propanol of >99% ee in the synthesis.

DETAILED DESCRIPTION OF THE INVENTION

The invention provides a scalable biocatalytic process for preparation of (S)-1,1,1-trifluoro-2-propanol by asymmetric microbial reduction of 1,1,1-trifluoroacetone with Baker's yeast with an enantiomeric purity of >99%, which comprises a) heating a suspension of Baker's yeast in 0.1–0.4M potassium phosphate buffer to a temperature of about 50–52° C. over a period of about 60 min, b) maintaining this suspension at a temperature of about 50–52° C. over a further period of about 90 min, c) diluting the heated suspension with buffer to a yeast concentration of about 20–30% w/v and cooling to a temperature of about 10° C. within a period of about 120 min, d) maintaining the pH of the suspension constant at 7.4 to 7.5 by automatic addition of 4M KOH solution over the whole process, e) adding 1,1,1-trifluoroacetone to a concentration of about 1–5% (w/v) at a temperature below the boiling point of 1,1,1-trifluoroacetone, f) reducing 1,1,1-trifluoroacetone to (S)-1,1,1-trifluoro-2-propanol at a temperature of about 20° C. within a period of about 5 to 8 days, and g) isolating the (S)-1,1,1-trifluoro-2-propanol by a sequence of distillation steps.

As used herein, the "Baker's yeast" is a cheap standard commercial baker's yeast, obtainable in bulk quantities, for example from Klipfel AG, Rheinfelden (Switzerland).

The preferred conditions for the process are individually as follows:

i) the biotransformation is carried out at room temperature over a time period of 5–8 days, ii) the buffer used is 0.1M phosphate buffer pH 7–8, iii) the substrate concentration is 2–4% w/v, iv) the substrate concentration is 3% w/v, v) the last distillation step is a rectification, vi) (S)-1,1,1-trifluoro-2-propanol is used as a building block for APIs in psychic disorders, vii) (S)-1,1,1-trifluoro-2-propanol is used as a building block for APIs as described in WO 2005/014563, viii) the APIs as described in WO 2005/014563 may be prepared with an isomeric purity of >99% ee.

The stereoselectivity of exceptionally cheap commercial Baker's yeast can be influenced by a defined heat treatment such that 1,1,1-trifluoroacetone can be reduced to (S)-1,1,1-trifluoro-2-propanol of high ee almost quantitatively.

No enzyme inhibitor and no coenzyme-regenerating system is required to achieve the desired high enantiomeric purity of >99%. Fortunately, the inactivation of the biocatalyst, the Baker's yeast, by this heat treatment is limited sufficiently so that still a technically relevant substrate concentration can be employed, and the amount of biomass (which has to be used to compensate for activity losses) is still acceptable for an efficient workup. Ethanol production during the biotransformation can be kept to a level that allows an efficient workup. Furthermore, a technically attractive product recovery process was developed, based solely on distillation.

The invention may be described in more detail as follows:

Scheme 1

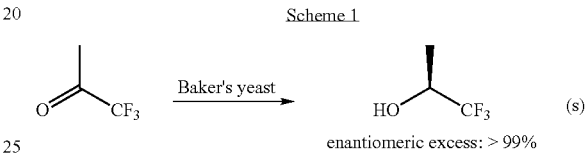

enantiomeric excess: > 99%

The obstacle of a highly stereoselective asymmetric reduction of 1,1,1-trifluoroacetone by Baker's yeast is—as partly shown by the cited references—the adverse effect of heat treatment: on one hand increasing stereoselectivity (by inactivating predominantly the less selective reducing enzymes) and on the other hand decreasing activity (by inactivating the selective enzyme(s)). This obstacle can be expected to be more pronounced at higher, technically more relevant (but physiologically less favourable) substrate concentrations.

In accordance with the invention, an extremely narrow bridge of conditions for a heat-treatment of Baker's yeast exists (50–52° C. for 90–240 min) that significantly reduces the activity of the unwanted enzyme(s) without affecting too much the activity and stability of the selective enzyme(s).

Such preconditioned Baker's yeast can then be used to prepare (S)-1,1,1-trifluoro-2-propanol by reduction of 1,1,1-trifluoroacetone—without using an additional enzyme inhibitor—with >99% ee, at a still technically relevant substrate concentration and an acceptable biomass concentration of 30% w/v yeast (10 times excess of yeast with respect to substrate) enabling a workup procedure with excellent yield.

The almost quantitative reduction of the substrate (1,1,1-trifluoroacetone)—without requiring a coenzyme-regenerating system—is likewise important for the process due to the high price of the substrate. There is a very narrow temperature range for the heat treatment between insufficient selectivity and catalyst inactivation.

Furthermore, because Baker's yeast is not only commercially available, no fermentation equipment is required to prepare the biocatalyst to perform the process, and it is also exceptionally cheap. This contributes additionally to the economy of the process.

The process can also be carried out using Baker's yeast from other manufacturers, for example from DSM (Dordrecht, The Netherlands), Proofex (Dublin, Ireland), S. I. de Leuvre Fala (Strasbourg, France), Suomen Hiiva Oy (Lahti, Finland) or Hefe Fabrik Giegold (Schwarzenbach, Germany). In all cases the enantiomeric excess of the TFIP produced in biotransformations following heat treatment at 50° C. is ≧99% (see Table below). That the heat treatment had a broadly similar effect on the selectivity of all yeasts tested indicates that any commercially available Baker's yeast can be used in the described process.

| Yeast Supplier | Heat Treatment | EtOH (g/L) | TFIP yield (%) | R-TFIP (%) | S-TFIP (%) |
|---|---|---|---|---|---|
| Klipfel | No | 1.1 | 94.8 | 2.1 | 97.9 |
| Klipfel | Yes | 0.7 | 73.5 | 0.2 | 99.8 |
| DSM | No | 5.0 | 88.3 | 3.1 | 96.1 |
| DSM | Yes | 6.3 | 67.8 | 0.4 | 99.6 |
| Proofex | No | 0.2 | 31.1 | 1.5 | 98.5 |
| Proofex | Yes | 0.0 | 38.8 | 0.4 | 99.6 |
| Fala | No | 5.3 | 96.9 | 2.2 | 98.8 |
| Fala | Yes | 3.1 | 80.2 | 0.2 | 99.8 |
| Suonenhiiva | No | 3.9 | 91.7 | 1.9 | 98.1 |
| Suonenhiiva | Yes | 4.2 | 64.7 | 0.5 | 99.5 |
| Giegold | No | 7.5 | 70.0 | 2.4 | 97.6 |
| Giegold | Yes | 4.7 | 42.0 | 0.6 | 99.4 |

The results have been achieved as follows:

50 g of each yeast was suspended to a final volume of 100 ml in 0.1 M potassium phosphate buffer pH 7.4 and transferred to 250 ml glass bottles. The suspended yeasts were subjected to heat treatment at 50° C. for 2 hours in a heated water bath. After cooling on ice the yeasts were diluted to 30% w/v with buffer. 2.5 ml aliquots were then transferred to 10 ml serum bottles and 86 ul of a 940 g/L solution of TFAC in water added to give a final concentration of 3% w/v. After closing with rubber seals the bottles were incubated for 6 days with rolling at 20° C. Periodically samples were removed and analyzed by GC and chiral GC for quantification of TFAC (1,1,1-trifluoroacetone), EtOH (ethanol) and TFIP (1,1,1-trifluoro-2-propanol) and determination of the enantiomeric excess of the product.

Furthermore, and not less important, the invention provides a simple and unexpectedly efficient workup procedure for recovering the product in high purity and yield out of this high-density biobroth. This process is based solely on distillation. No extraction solvent is used for recovering the product.

The complete process for preparation of (S)-1,1,1-trifluoro-2-propanol (Scheme 1) can be subdivided formally into three steps:

1. Pre Treatment of Baker's Yeast

The yeast (2–4 kg) is suspended in potassium phosphate buffer (pH=7.4) and the suspension brought to the desired final volume of 6 L. The suspension is heated to a temperature of about 50° C. over a period of about 60 min and held at this temperature for a further period of about 90 min. After 90 min heating is stopped, and a further portion of cold potassium phosphate buffer is added to adjust the yeast concentration to about 30% w/v. The suspension is cooled to a temperature of about 5–20° C. over a period of about 90 min.

2. Biotransformation 1,1,1-Trifluoroacetone (0.15–0.3 kg) is added to the cooled yeast suspension obtained in step 1, and the temperature is brought to about 20° C. In order to keep the ethanol concentration in the reaction broth low, the pH is maintained at 7.4 to 7.5 by the controlled addition of 4M KOH solution. Due to the very similar boiling points of (S)-1,1,1-trifluoro-2-propanol (bp. 76–77° C.) and of ethanol (bp. 78° C.), a low concentration of ethanol in the reaction mixture is essential to isolate (S)-1,1,1-trifluoro-2-propanol free of ethanol in high yield. This aspect is an essential part of this procedure.

Optionally, the substrate can be added in a fed-batch type process.

The substrate concentration used in the present process is significantly higher than those described in the prior art. This higher volumetric productivity results in considerable cost savings due to the requirement for smaller reaction volumes and to product isolation. A practically complete conversion of the substrate can be accomplished in a reaction time of about 5–8 days.

3. Isolation and Purification of (S)-1,1,1-Trifluoro-2-Propanol (S)-1,1,1-trifluoro-2-propanol is isolated from the biobroth obtained in step 2. In the $1^{st}$ batch distillation, the product volume is reduced by a factor of 10, and an aqueous TFIP solution of approximately 25% w/w is obtained. Unexpectedly, in spite of the high biomass content (employed to compensate for the loss of enzyme activity) of the biobroth, the product can be recovered in practically quantitative yield.

In the $2^{nd}$ batch distillation over sodium chloride, the water content of the product is further reduced to afford a product of approximately 90% m/m. Alternatively, the $2^{nd}$ batch distillation can be performed without sodium chloride, affording a product of approximately 80% w/w.

In the $3^{rd}$ distillation, rectification on a packed column, unwanted side products such as traces of non-reacted 1,1,1-trifluoroacetone and ethanol are removed. Purified (S)-1,1,1-trifluoro-2-propanol is obtained as 95% w/w product, with 5% water and <0.2% of organic impurities. The content of ethanol is critical (as it might react in the subsequent reaction step as well and impair the purity of the API) and should be <0.5% (w/w) which is rather a challenge for biotransformation and workup.

Optionally, anhydrous (S)-1,1,1-trifluoro-2-propanol can be prepared by introducing a drying step with a molecular sieve before or after the last distillation step, or by using extractive distillation or pervaporation.

Increasing the yeast concentration to about 60% w/v leads to a significant reduction in the reaction time (factor 2) needed to achieve 95% yield, which potentially leads to cost savings on production scale. Effects of doubling the yeast concentration from 30% w/v to 60% w/v in biotransformations on the 10 L scale are shown in the table below:

| Experiment | Yeast concentration (w/v) | Reaction time (h) | Biotransformation yield (%) |
|---|---|---|---|
| A | 30% | 66 | 78 |
|   |     | 138 | 94 |
| B | 30% | 66 | 84 |
|   |     | 138 | 95 |
| C | 60% | 66 | 96 |
|   |     | 138 | — |
| D | 60% | 66 | 98 |
|   |     | 138 | — |

As mentioned above, the obtained (S)-1,1,1-trifluoro-2-propanol can be used as a building block for the preparation of pharmaceutically active compounds having an S-configurated 1,1,1-trifluoropropan-2-yl ether moiety. As an example, Scheme 2 shows the preparation of pharmaceutically active compounds that are inhibitors of the glycine transporter using such building block. These compounds are disclosed in WO 2005/014563.

The compounds prepared in Scheme 2 contain an (S)-configurated 1,1,1-trifluoropropan-2-yl ether moiety which is introduced into the molecule via the (S)-1,1,1-trifluoro-2-propanol building block in the penultimate synthesis step in one branch of a convergent synthesis (see Scheme 2).

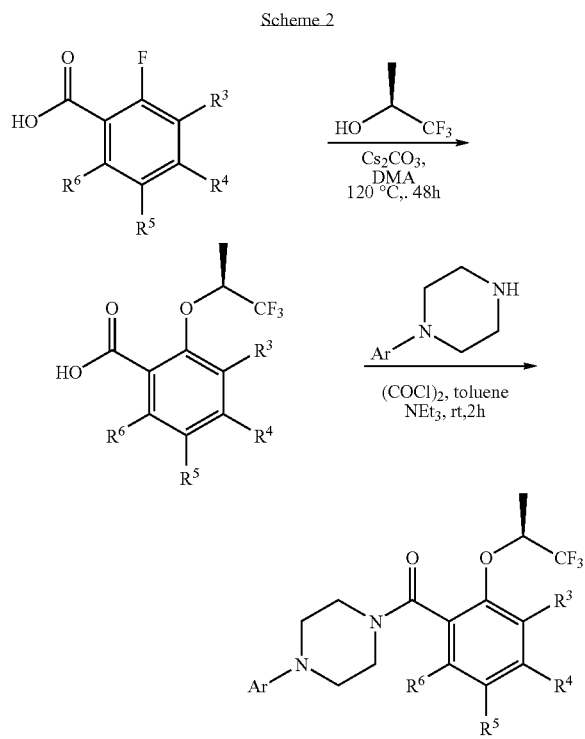

Scheme 2

No crystallization procedure has been found so far to enantiomerically enrich the intermediates through to the API. Therefore, it is paramount to use (S)-1,1,1-trifluoro-2-propanol of an enantiomerical purity >99% for the synthesis of the APIs.

EXAMPLES

Laboratory Scale

Example 1

(Pre-Treatment of Baker's Yeast)

3.0 kg of Baker's yeast (Blockhefe of Klipfel AG, Rheinfelden, Switzerland; product no. 101010) was dispersed in 0.1M potassium phosphate buffer pH 7.4 and the volume made up to 6 L (50% w/v) with the same buffer. The suspended yeast was then transferred to a 15 L temperature controlled glass reactor. A top mounted stirrer was used for mixing (200 rpm). The yeast suspension was then heated from ambient temperature to 50° C. in a period of 60 min and the temperature held at this value for a further 90 min. At this point heating was stopped. A further 4 L of cold buffer (4° C.) was added to bring the total volume to 10 L (30% w/v yeast). The broth was cooled to 10° C. over a period of about 90 min. A pH value of 7.4 to 7.5 was maintained by automatic addition of 4M KOH solution using a pH-stat.

| Heat treatment | | |
|---|---|---|
| Time (min) | Temperature (° C.) | 4M KOH solution consumed (g/L) |
| 0 | 24.3 | 2 |
| 20 | 35.0 | 2.6 |
| 45 | 47.8 | 4 |
| 60 | 49.2 | 5.8 |
| 90 | 49.4 | 10.4 |
| 150 | 49.4 | 16.8 |
| 160 | 43.3 | n.d. |
| 170 | 28.9 | 19.6 |
| 195 | 24.3 | 21.2 |
| 215 | 18.3 | 24.2 |
| 245 | 11.2 | 26.2 |

Example 2

(Biotransformation)

304 g 1,1,1-Trifluoroacetone was added to the cooled broth (10 L), and the temperature was held at 20° C. for the duration of the reaction which was 5 days in this case. The reaction broth in the vessel was continuously overlaid with nitrogen (safety reasons). The pH was maintained at 7.4 to 7.5 by automatic addition of 4M KOH solution from a pH-stat. Periodically, samples were removed and analyzed by GC and chiral GC for quantification of TFAC (1,1,1-trifluoroacetone), EtOH (ethanol) and TFIP (1,1,1-trifluoro-2-propanol) and determination of the enantiomeric excess of the product.

| Biotransformation | | | | | |
|---|---|---|---|---|---|
| Reaction Time (h) | TFAC (g/L) | EtOH (g/L) | TFIP (g/L) | R-TFIP (%) | S-TFIP (%) |
| 1 | 23.0 | 2.3 | 0.7 | | |
| 2.5 | 19.5 | 2.8 | 2.8 | | |
| 71 | 4.6 | 2.4 | 21.5 | 0.4 | 99.6 |
| 90 | 2.5 | 2.5 | 24.1 | | |
| 96.5 | 3.1 | 2.2 | 24.0 | | |
| 117 | 2.7 | 2.3 | 24.7 | | |
| 144 | 2.4 | 2.0 | 24.0 | | |

Example 3

(Isolation of (S)-1,1,1-Trifluoro-2-Propanol from the Biobroth and its Enrichment)

10.9 kg biobroth was transferred to a Büchi R152 rotavapor with 20 L round bottom flask, equipped with a cold trap (dry ice). The distillation was performed at 60° C. bath temperature at 140 mbar vacuum and at 15° C. condenser temperature. The observed distillation temperature was 55° C. Fraction 1 (see below) was combined with the product obtained in the cold trap (biphasic solution). The composition of the products was analyzed by GC.

| 1st distillation | | | | |
|---|---|---|---|---|
| Product description | Weight (g) | TFAC (g) | EtOH (g) | TFIP (g) |
| Biobroth | 10919.0 | 26.2 | 21.8 | 262.2 |
| Fraction 1 & Cold trap product | 1001.9 | 20.7 | 4.7 | 258.8 |
| Fraction 2 | 548.4 | 4.3 | 3.4 | 1.0 |
| Distillation sump | 9539.0 | 1.2 | 13.8 | 2.5 |

To the product from the 1st distillation (fraction 1 and product from cold trap) was added 300 g sodium chloride, and the mixture was stirred for one hour. A mixture of TFIP, aqueous phase and sodium chloride was obtained. The whole mixture was transferred to a Büchi R124 rotavapor with a 2 L round bottom flask. The distillation was performed at 90–98° C. bath temperature at ambient pressure and at 15° C. condenser temperature. A first TFIP fraction was obtained at 82–85° C., a second fraction at 85–98° C.

| 2nd distillation | | | | | |
|---|---|---|---|---|---|
| Product description | Bp. (° C.) | Weight (g) | TFAC (g) | EtOH (g) | TFIP (g) |
| Product 1st distillation/NaCl | | 1301.9 | 20.7 | 4.7 | 258.8 |
| Fraction 1 | 82–85 | 287.1 | 12.2 | 7.8 | 254.6 |
| Fraction 2 | 85–98 | 9.2 | 0.3 | 0.5 | 7.5 |

The product obtained by combining fractions 1 and 2 was used for the final distillation.

Example 4

(Final Purification of (S)-1,1,1-Trifluoro-2-Propanol)

625 g enriched (S)-1,1,1-trifluoro-2-propanol, obtained after the 2nd distillation from two biotransformation reactions on the 10 L scale, was used for the final fractional distillation. The distillation was carried out using a 1 L round bottom flask connected to a 5×150 cm distillation column (Sulzer packing BX). The column was equipped with a reflux divider on the top. The distillation was performed at 150° C. bath temperature at ambient pressure and at 5° C. condenser temperature. The selected reflux ratio (1:20 to 1:99) was dependant on the obtained product quality (by monitoring on GC). The time for distillate withdrawal was 1 second.

| 3rd distillation | | | | | | |
|---|---|---|---|---|---|---|
| Product description | RLV | Bp. (° C.) | Weight (g) | TFAC (g) | EtOH (g) | TFIP (g) |
| Starting material | — | | 624.6 | 9.11 | 37.58 | 546.6 |
| Fraction 1 | 1:20 | 59.0–76.4 | 86.0 | 8.69 | 0.08 | 76.0 |
| Fraction 2 | 1:20 | 76.4–76.7 | 49.5 | 0.61 | 0.00 | 49.1 |
| Fraction 3 | 1:20 | 76.7–76.8 | 49.1 | 0.28 | 0.00 | 50.3 |
| Fraction 4 | 1:20 | 76.8–76.9 | 51.4 | 0.15 | 0.00 | 54.4 |
| Fraction 5 | 1:20 | 76.9 | 47.7 | 0.08 | 0.00 | 50.9 |
| Fraction 6 | 1:20 | 76.9 | 46.9 | 0.05 | 0.00 | 48.99 |
| Fraction 7 | 1:40 | 76.9 | 26.4 | 0.02 | 0.02 | 27.56 |
| Fraction 8 | 1:40 | 76.9–77.0 | 28.3 | 0.04 | 0.04 | 28.62 |

-continued

| 3rd distillation | | | | | | |
|---|---|---|---|---|---|---|
| Product description | RLV | Bp. (° C.) | Weight (g) | TFAC (g) | EtOH (g) | TFIP (g) |
| Fraction 9 | 1:40 | 77.0–77.4 | 33.7 | 0.03 | 0.18 | 35.01 |
| Fraction 10 | 1:40 | 77.4–78.2 | 22.7 | 0.02 | 0.49 | 23.51 |
| Fraction 11 | 1:40 | 78.2–78.3 | 3.26 | 0.01 | 0.14 | 2.88 |
| Fraction 12 | 1:99 | 78.3–79.1 | 31.8 | 0.04 | 2.42 | 27.36 |
| Fraction 13 | 1:99 | 79.1–79.3 | 23.1 | 0.02 | 3.27 | 16.81 |
| Distillation sump | — | | 108.4 | 0.35 | 35.87 | 64.39 |

The final product obtained by combining fractions 2 to 8 (299 g) showed the following analytical data:

Identity by NMR (CDCl$_3$) and HPLC/MS: in accordance;

composition (GC): 94.8% w/w TFIP, 0.4% w/w TFAC, 0.02% w/w ethanol;

water content (Karl-Fisher): 4.8% w/w;

enantiomeric excess (chiral GC): 99.3%.

Large Scale Preparation

Example 5

(Pre-Treatment of Baker's Yeast)

a) Heat-Treatment of Baker's Yeast:

An 800 L stainless steel reaction vessel was filled with 240 L 0.1 M phosphate buffer pH 7.5 cooled to 10° C. The buffer was prepared by dissolving 10.88 kg potassium dihydrogen phosphate (product no. 60220; Fluka/Switzerland) and 4.08 kg potassium hydroxide (product no. 60370; Fluka/Switzerland) in 804 L deionized water. 240 kg Baker's yeast (product no. 104020, "Sackhefe; Klipfel" AG, Rheinfelden/Switzerland) was added with stirring. The mixture was further stirred at 10° C. for 60 min to homogenize the yeast suspension. A temperature probe dipping into the suspension was installed, and the reactor was inertized. The yeast suspension was heated to 50.3° C. (+/−0.5° C.) within 83 min and held at 50.3° C. (+/−0.5° C.) for 90 min. Then 320 L 0.1 M phosphate buffer pH 7.5 of 10° C. was added, and the mixture was cooled to 10° C. within 67 min. During heat-treatment the pH-value of the suspension was held at pH 7.5 by controlled (pH-stat) addition of a 50% potassium hydroxide solution (12.0 kg). The prepared yeast suspension was stored temporarily at 10° C. in the reaction vessel for 25 h, maintaining pH 7.5 control (5.8 kg 50% potassium hydroxide solution consumed).

b) Use-Test of Heat-Treated Baker's Yeast:

A use-test was performed to verify the desired activity/stereoselectivity of the prepared yeast prior to addition of the expensive 1,1,1-trifluoroacetone. 2 L of the heat-treated yeast suspension was placed in a 2 L laboratory glass reactor. 60 g 1,1,1-trifluoroacetone were added with stirring to the cooled (10° C.) suspension. The reaction mixture was subsequently heated to 21° C. within 60 min. During the biotransformation the pH-value of the reaction mixture was held at pH 7.5 by controlled (pH-stat) addition of a 25% potassium hydroxide solution (16 g added within 20 h). (S)-1,1,1-trifluoro-2-propanol was obtained in 32% yield and 99.2% ee after 20 h reaction time (test criteria: >25% yield and >98.9% ee after 15–30 h reaction time).

Example 6

(Biotransformation)

24.7 kg ice-cold 1,1,1-trifluoroacetone was transferred via a dip tube within 55 min to the cooled (10° C.) yeast suspension with stirring. After stirring for an additional 20 min, the temperature of the reaction mixture was increased to 20° C. within 55 min. During the biotransformation, the pH-value of the reaction mixture was held at pH 7.5 by controlled (pH-stat) addition of a 50% potassium hydroxide solution (16.8 kg consumed within 159 h). (S)-1,1,1-trifluoro-2-propanol was obtained in 96% yield and 99.4% ee after 159 h reaction time. 860 kg reaction mixture was obtained. The reaction mixture was then stored for 1 day at 20° C. and 3 days at 6° C. prior starting distillative product recovery.

Example 7

(Isolation of (S)-1,1,1-Trifluoro-2-Propanol from the Biobroth and its Enrichment)

a) First Distillation:

The distillation was performed out of the reaction vessel which was equipped with a condenser. The distillation was run at 60° C. jacket temperature, 140 mbar pressure and 6–8° C. condenser temperature. To prevent excessive foaming 0.5 kg Basildon antifoam (product no. BC 86/013; Basildon chemical Company Ltd/England) was added. The product composition was analyzed by GC. The distillation afforded 101 kg step-1 product, incl. product in the dry ice cold trap. The product composition was 19.8 m/m-% 1,1,1-trifluoro-2-propanol, 0.2% 1,1,1-trifluoroacetone, 2.5% ethanol and 77.5% water.

b) Second Distillation:

The distillation of the step-1 product was done in three batches of each approx. 30 L on a Büchi R187 rotavapor with a 50 L distillation flask. At a bath-temperature of 90° C. and a condenser temperature of 12–15° C., a first fraction was taken at normal pressure until the head temperature dropped to <60° C. A second fraction was taken at 700 mbar and a third fraction at 500 mbar. The quality of the obtained fractions was analyzed with GC and pooling of appropriate fractions was done according a preset purity criterium using excel calculation (ratio of 1,1,1-trifluoro-2-propanol to ethanol >15). In total 28.5 kg step-2 product was obtained. The product composition was 79.3 m/m-% (S)-1,1,1-trifluoro-2-propanol, 0.7% 1,1,1-trifluoroacetone, 4.9% ethanol and 15.2% water.

c) Third Distillation:

The distillation of the step-2 product was carried out in two batches of each approx. 14 kg on a 5×150 cm rectification column (Sulzer packing BX) with a 20 L round bottom flask. The column was equipped with a reflux divider on the top. The distillation was performed at 115° C. bath temperature, ambient pressure and 5° C. condenser temperature. The selected reflux ratio (1:10 to 1:50) was dependant on the obtained product quality (by monitoring on GC). The time for distillate withdrawal was 1 sec. Pooling of appropriate pure product fractions was done according to preset purity criteria using excel calculation. Pure (S)-1,1,1-trifluoro-2-propanol, containing 5% azeotropic water and <0.1% ethanol, was distilled at 76.7° C. to 76.8° C. The distillation in two batches afforded 20.5 kg step-3 product (criteria: ≧90% (S)-1,1,1-trifluoro-2-propanol, ≦0.5% ethanol) and 2.2 kg step-3 side product (criteria: ≧80% (S)-1,1,1-trifluoro-2-propanol, ≦5% ethanol) that in turn yielded another 1.4 kg step-3 product after redistillation. In total, the fractional distillation afforded 21.8 kg purified (S)-1,1,1-trifluoro-2-propanol.

Properties of Produced (S)-1,1,1-Trifluoro-2-Propanol:

The pooled product from the distillations (21.8 kg) showed following analytical data:

Identity by NMR (CDCl$_3$) and HPLC/MS: in accordance;

composition (GC): 95.1% w/w TFIP, <0.1% w/w TFAC, <0.1% w/w ethanol;

water content (Karl-Fisher): 5.2% w/w;

enantiomeric excess (chiral GC): 99.4%.

References:

Crawford, J. W. C. *Journal of the Chemical Society (C)* (1967), 2332–2333: Resolution of 1-trifluoromethylethanol. Part II.

Rosen T. C., Daussmann T., *Chimica Oggi* (2004) Suppl, 43–45: Biocatalyst vs. chemical catalyst for asymmetric reduction. Product list (2004) of Jülich Fine Chemicals GmbH, Jülich (Germany).

Bucciarelli M., Forni A., Moretti I. and Torre G., *Synthesis* (1983) 11, 897–899: Asymmetric reduction of trifluoromethyl and methyl ketones by yeast; an improved method.

Dahl A. C., Fjeldberg M. and Madsen J. O., *Tetrahedron: Asymmetry* (1999) 10, 551–559: Baker's yeast: improving the D-stereoselectivity in reduction of 3-oxo esters.

Yasohara Y., Kizaki N., Hasegawa J., Takahashi S., Wada M., Kataoka M., Shimizu S., *Appl Microbiol Biotechnol* (1999) 51: 847–851: Synthesis of optically active ethyl 4-chloro-3-hydroxybutanoate by microbial reduction.

Yang Z.-H., Yao S.-J. and Lin D.-Q., *Ind. Eng. Chem. Res.* (2004) 43, 4871–4875: Improving the stereoselectivity of asymmetric reduction of 3-oxo ester to 3-hydroxy ester with pretreatments on bakers' yeast.

Nakamura K., Kondo S., Kawai Y., Hida K., Kitano K. and Ohno A., *Tetrahedron: Assymmetry* (1996) 7, 409–412: enantio- and regioselective reduction of alpha-diketones by baker's yeast.

The invention claimed is:

1. A scalable biocatalytic process for the preparation of S-1,1,1-trifluoro-2-propanol with an enantiomeric excess of >99% by asymmetric microbial reduction of 1,1,1-trifluoroacetone with Baker's yeast, comprising
   a) heating a suspension of Baker's yeast in 0.1–0.4 M phosphate buffer to a temperature of about 50–52° C. over a period of about 60 min,
   b) maintaining this suspension at a temperature of about 50–52° C. over a further period of about 90 min,
   c) diluting the heated suspension with buffer to a yeast concentration of about 20–30% w/v and cooling to a temperature of about 10° C. within a period of about 120 min,
   d) maintaining the pH constant at 7.4 to 7.5 by automatic addition of 4 M KOH solution over the whole process,
   e) adding 1,1,1-trifluoroacetone to a concentration of about 1–5% (w/v) at a temperature below the boiling point of 1,1,1-trifluoroacetone,
   f) reducing 1,1,1-trifluoroacetone to (S)-1,1,1-trifluoro-2-propanol at a temperature of about 20° C. within a period of about 5 to 8 days, and
   g) isolating the (S)-1,1,1-trifluoro-2-propanol by a sequence of distillation steps.

2. The biocatalytic process of claim 1, wherein step e) is performed at room temperature over a time period of about 5–8 days.

3. The biocatalytic process of claim 1, wherein the phosphate is 0.1M phosphate buffer having pH 7–8.

4. The biocatalytic process of claim 1, wherein the concentration of 1,1,1-trifluoroacetone is about 2–4% w/v.

5. The biocatalytic process of claim 4, wherein the concentration of 1,1,1-trifluoroacetone is 3% w/v.

6. The biocatalytic process of claim 1, wherein the last distillation step in step g) is a rectification.

7. The biocatalytic process of claim 1, wherein the distillation in step g) consists of three distinct distillations.

8. The biocatalytic process of claim 7, wherein the second distillation step is distillation over sodium chloride.

9. The biocatalytic process of claim 8, wherein the third distillation step is a rectification.

10. The biocatalytic process of claim 7, wherein the third distillation step is a rectification.

* * * * *